(12) United States Patent
Noe'

(10) Patent No.: US 6,252,074 B1
(45) Date of Patent: Jun. 26, 2001

(54) PROCESS AND APPARATUS FOR MELAMINE MANUFACTURE

(75) Inventor: Sergio Noe', San Donato Milanese (IT)

(73) Assignee: Eurotecnica Development & Licensing S.r.l., Milan (IT)

( * ) Notice: Subject to any disclaimer, the term of this patent is extended or adjusted under 35 U.S.C. 154(b) by 0 days.

(21) Appl. No.: 09/446,814

(22) PCT Filed: Jun. 16, 1998

(86) PCT No.: PCT/IT98/00161

§ 371 Date: Dec. 23, 1999

§ 102(e) Date: Dec. 23, 1999

(87) PCT Pub. No.: WO99/00374

PCT Pub. Date: Jan. 7, 1999

(30) Foreign Application Priority Data

Jun. 27, 1997 (IT) .............................. MI97A1524

(51) Int. Cl.⁷ ....................... C07D 251/60; C07D 251/62
(52) U.S. Cl. ............................................... 544/201
(58) Field of Search ................................. 544/201

(56) References Cited

U.S. PATENT DOCUMENTS 3,116,294 * 12/1963 Marullo et al. ...................... 544/201
3,143,394 * 8/1964 Mallison ............................. 544/201
5,721,363 * 2/1998 Canzi et al. ......................... 544/201

FOREIGN PATENT DOCUMENTS 96 20182 * 7/1996 (WO) .

* cited by examiner

*Primary Examiner*—Richard L. Raymond
(74) *Attorney, Agent, or Firm*—Pauley Petersen Kinne & Fejer

(57) ABSTRACT

High pressure melamine manufacturing process starting from urea with high yields and conversion rates characterized in that it comprises the following steps: a) urea is fed to a reactor essentially containing molten melamine, which reactor operates in continuous and is kept at a temperature in the range of 360 to 420° C. under a pressure higher than $7 \times 10^3$ KPa and preferably $8 \times 10^3$ to $9 \times 10^3$ KPa, while a vigorous mixing is provided by evolving gases; b) liquid reaction product is recovered containing 85 to 95%, preferably 88 to 93% melamine and a gaseous phase is removed containing essentially $CO_2$ and $NH_3$; c) liquid phase collected in b) is continuously fed, together with fresh $NH_3$ to a tubular reactor, in which the essentially whole volume is occupied by the liquid phase (plug flow reactor) without any mixing of the reaction product with reactant nor the intermediate products (no "back mixing"), kept at a temperature of 360 to 450° C. and under a pressure higher than $7 \times 10^3$ KPa for a residence time sufficient to complete the reaction; d) melamine with a high purity level is collected from the outlet of the tubular reactor.

13 Claims, 2 Drawing Sheets

PROCESS AND APPARATUS FOR MELAMINE MANUFACTURE

BACKGROUND OF THE INVENTION

1. Field of the Invention

This invention relates to a process for high yield manufacture of high purity melamine and the apparatus to carry out the process.

More particularly this invention is directed to melamine preparation starting from urea using a high pressure process.

2. Description of Prior Art

Melamine is presently manufactured from urea according to the following simplified reaction scheme:

$$6CO(NH_2)_2 \longrightarrow \text{melamine} + 6NH_3 + 3CO_2 \quad (A)$$

(melamine = $C_3N_3(NH_2)_3$)

The reaction is highly endothermic, the reaction heat at a temperature of 360 to 420° C. being approximately 93,000 Kcalories per Kmole of melamine.

The process can be carried out at low pressure in presence of catalysts or at high pressure without any catalyst.

Both low pressure and high pressure melamine manufacturing processes starting from urea are believed to proceed through a series of intermediate reactions leading to, respectively, isocyanic acid, cyanuric acid, ammelide, ammeline and finally melamine. It seems that the following reactions are involved:

$$3CO(NH_2)_2 \longrightarrow 3HOCN + 3NH_3 \quad (1)$$
$$\text{urea} \qquad \text{isocyanic ac.}$$

$$3HOCN \longrightarrow C_3N_3(OH)_3 \quad (2)$$
$$\text{cyanuric ac.}$$

$$C_3N_3(OH)_3 + NH_3 \longrightarrow C_3N_3(OH)_2NH_2 + H_2O \quad (3)$$
$$\text{ammelide}$$

$$C_3N_3(OH)_2NH_2 + NH_3 \longrightarrow C_3N_3(OH)(NH_2)_2 + H_2O \quad (4)$$
$$\text{ammeline}$$

$$C_3N_3(OH)(NH_2)_2 + NH_3 \longrightarrow C_3N_3(NH_2)_3 + H_2O \quad (5)$$
$$\text{melamine}$$

$$3CO(NH_2)_2 + 3H_2O \longrightarrow 6NH_3 + 3CO_2 \quad (6)$$

By summing up equations 1 to 6 the overall reaction of equation (A) is obtained.

Some of these intermediate products, namely ammeline and ammelide, hereinafter collectively referred to as OAT (OxyAminoTriazine), have been detected in the reaction products.

Moreover melamine, obtained as above, reacts with itself under reaction temperature and pressure yielding so-called polycondensates and a release of ammonia. Polycondensates, beyond being impurities reducing melamine purity degree, also decrease overall reaction yields.

Polycondensates result from amine group (—$NH_2$) ammonolysis of the melamine molecule and are formed, for example, according to the following 2 melamine $\longleftrightarrow$ Melem + $NH_3$ 2 melamine $\longleftrightarrow$ Melem + 2$NH_3$ The above reactions are promoted by a low or nonexistent ammonia partial pressure and the long residence time of melamine in the liquid phase ($\geq 355°$ C.). Under the melamine synthesis conditions, polycondensates are obtained in a low amount; however such an amount is not negligible with respect to the final product purity. Anyhow an almost complete polycondensate to melamine regression is achieved by increasing ammonia partial pressure. In conventional melamine synthesis processes, polycondensates conversion to melamine takes place in the melamine purification section wherein, inter alia, an ammonia treatment of the reaction product is provided for.

In the high pressure process, molten urea at a temperature of 140 to 150° C. is fed to a reactor, kept at a temperature of 360 to 420° C. by means of suitable heating devices. In this reactor, molten urea mixes with melamine and remains under stirring actions of the evolving reaction gases for a determined period of time. Raw melamine product is subject to a purification treatment, for instance by dissolving it in water, and subsequent recrystallization to eliminate unreacted urea and remove reaction by-products essentially consisting of reaction gaseous products (ammonia and carbon dioxide), liquid reaction products essentially comprising OAT (mainly ammeline) and polycondensates.

In the industrial process embodiments, reaction is carried out in continuous manner, typically in a single reactor consisting of a cylindrical vessel (tank reactor) wherein the reactants are kept under vigorous mixing by the generation and evolution of reaction gaseous products. Reaction heat is supplied to reactants through suitable heat exchange tubes in which molten salts circulate at a temperature higher than the reaction temperature.

Inside the reactor, each chemical species concentration exhibits a constant value almost in any point of the liquid reaction mixture. Molten urea, continuously fed to the reaction zone, immediately mixes with circulating, reaction mixture. The reaction product is continuously removed and it has the same concentration as the reaction mixture in the reactor. In said reaction arrangement, the higher is the desired conversion rate, and the lower is the melamine production rate. Therefore large reaction volumes are required resulting in a very expensive operation in that the reactor has to be resistant to the highly corrosive action of the reactants and reaction products under very severe temperature and pressure conditions. As a consequence, the costs of the material of the reactor and its working are extremely high.

Even if the reactor had a reactor volume sufficient to achieve approximately a 100% conversion ratio, by remarkably increasing in such a way the reactor costs, it would not be possible to manufacture melamine at a purity degree as required by the market. As a matter of fact, on one side, even optimizing the mixing of reaction mixture, it is not possible to prevent part of the reactants (urea) from coming out of the reactor before the necessary residence time is elapsed to enable its complete dissolution into the liquid mass and its complete conversion to melamine. The smaller is the reaction volume the more is the content of unreacted components which is present in the reaction mixture. Moreover unreacted component content increases, depending on the departing of the reaction mixture from the ideal mixing conditions. On the other side, the residence time distribution in the reaction is such that roughly one half of the reactant mixture remains inside the reactor for a period of time longer than the average residence time, i.e. the ratio between the reactor volume and reactant volume flow rate. Since the reaction mixture practically consists of melamine only, it is subject for a long period of time to ammonolysis reaction resulting in an increased amount of polycondensates.

Therefore, single reactor melamine manufacturing processes yield low purity degree melamine (lower than 97–98%) suitable for marginal uses only, unless the reaction product is submitted to purification treatments affecting the process overall economy, to reach high purity melamine (higher than 99.5%).

Multiple reaction section melamine synthesis processes have been proposed which allow increases in melamine purity. An example of a two-step melamine synthesis process has been disclosed in U.S. Pat. No. 3,116,294. However, since the second reactor employed in the second step is analogous to the first, i.e. both are tank reactors, same drawbacks are experienced, even of a less importance, as in the single reactor process.

SUMMARY OF THE INVENTION

It would be highly desirable to have available a high yield and conversion, high purity melamine manufacturing process which does not require expensive apparatuses.

It is therefore an object of the present invention to provide a high pressure melamine manufacturing process starting from urea, which process enables with high conversions a high purity product that may be employed as such, or after a simple purification, for most of the conventional uses. A further object of the present invention is to provide an apparatus for carrying out the above process.

These and other objects of the present invention are addressed by a reaction system carried out in two or more consequent reaction steps wherein, from the first step through the latter step, the reaction parameters, such as reaction overall pressure and temperature, and gaseous product partial pressures, are progressively changed. Residence times are thoroughly controlled especially in the last reaction steps in order to accomplish the complete reaction and the relevant disappearance of by-products with an increased yield.

More particularly, the high-pressure melamine manufacturing process starting from urea according to the present invention comprises the following steps:

a) urea is fed to a reactor essentially containing molten melamine, which reactor operates in continuous manner and is kept at a temperature in the range of 360 to 420° C. under a pressure higher than $7 \times 10^3$ kPa and preferably $7 \times 10^3$ to $9 \times 10^3$ kPa, while vigorous mixing is provided by the evolving gases;

b) liquid reaction product is recovered containing 85 to 95%, preferably 88 to 93% melamine and a gaseous phase is removed containing essentially $CO_2$ and $NH_3$;

c) liquid phase collected in step b) is continuously fed, together with fresh $NH_3$, to a tubular reactor in which essentially the whole volume is occupied by the liquid phase (plug flow reactor) without any mixing of the reaction product with reactants nor the intermediate products (no "back mixing"), kept at a temperature of 360 to 450° C. and under a pressure higher than $7 \times 10^3$ kPa for a residence time sufficient to complete the reaction; and d) melamine with a purity level higher than 99.5, not including any dissolved gaseous phase, is collected from the outlet of the tubular reactor.

The liquid phase entering the tubular reactor, according to step c) above, passes through the entire reactor length within a precisely defined period of time corresponding to residence time defined by the ratio between tubular reactor length and liquid reacting mixture linear velocity through the reactor itself.

The process according to the present invention enables production of a high purity melamine with high reaction yield by using a standard type tank reactor where at least one tubular reactor, as above defined, is connected downstream of the standard reactor.

The process according to the present invention can be applied to existing melamine manufacturing plants to obtain higher yields and purity level of the product.

It is apparent that the process of the invention may be applied to new melamine synthesis plants. In such cases, the process of the invention enables production of melamine having higher yields and purity degree using a smaller size tank reactor which is the more expensive equipment of the overall unit.

The amount of fresh ammonia to be fed to the tubular reactor together with the reaction liquid mixture from step b) is higher than the sum of the amount corresponding to liquid mixture saturation plus the stoichiometric amount necessary to convert all OAT and all condensates to melamine. The amount of ammonia is such as to ensure substantial excess ammonia within the liquid phase.

According to another embodiment of the present invention, the second step of the reaction is divided in two sections. At the end of the first section, a gaseous phase, essentially comprising ammonia, carbon dioxide and melamine vapor traces, is removed and molten melamine is fed, together with fresh ammonia and after removal of dissolved carbon dioxide, to the second reaction section comprising a tubular reactor similar to the first section. In this second reaction section, the pressure within the tubular reactor is higher than the pressure of both the first reactor (tank reactor) and the first section of the second reaction step.

A further embodiment of the high yield melamine manufacturing process according to the invention comprises the addition of a third section to the second step of the reaction similar to the second section. However, said addition is generally not necessary in that the process according to the invention wherein the second reaction step comprises one or two reaction sections, can produce a very high purity. The configuration with three or more sections in the second reaction step could be useful only in case a nearly 100% melamine purity is sought.

Gaseous phase removed from the reaction product both in the final and intermediate stages may be sent to urea synthesis, after gaseous melamine recovery; alternatively a portion of the ammonia present in said gaseous phase may be separated and used in the process.

The tubular reactor employed in the second step of the process according to the present invention comprises geometrical parameters to ensure a Reynolds number higher than 5,000, preferably higher than 10,000.

The heating means of the step a) reactor is quite conventional and may consist of molten salt heating coils arranged inside the reactor. The step c) tubular reactor of step c) can be heated by a molten salt bath.

Temperature inside the "plug flow" tubular reactor may be the same as that of the tank reactor, but preferably is higher than that in order to shorten reactant residence times and ensure reaction completeness.

Melamine recovered at the outlet of the tubular reactor exhibits purity higher than 99.5%, as a result of which it may be directly used after cooling and stripping out of dissolved gaseous phase without any additional treatments.

BRIEF DESCRIPTION OF THE DRAWINGS

These and other objects and features of the invention will be better understood from the following detailed description taken in conjunction with the drawings wherein.

Examples and drawings are intended to better explain how to practice the invention and the advantages thereof, but they are not to be interpreted as limiting its scope.

DESCRIPTION OF PREFERRED EMBODIMENTS

EXAMPLE I

Figure 1:
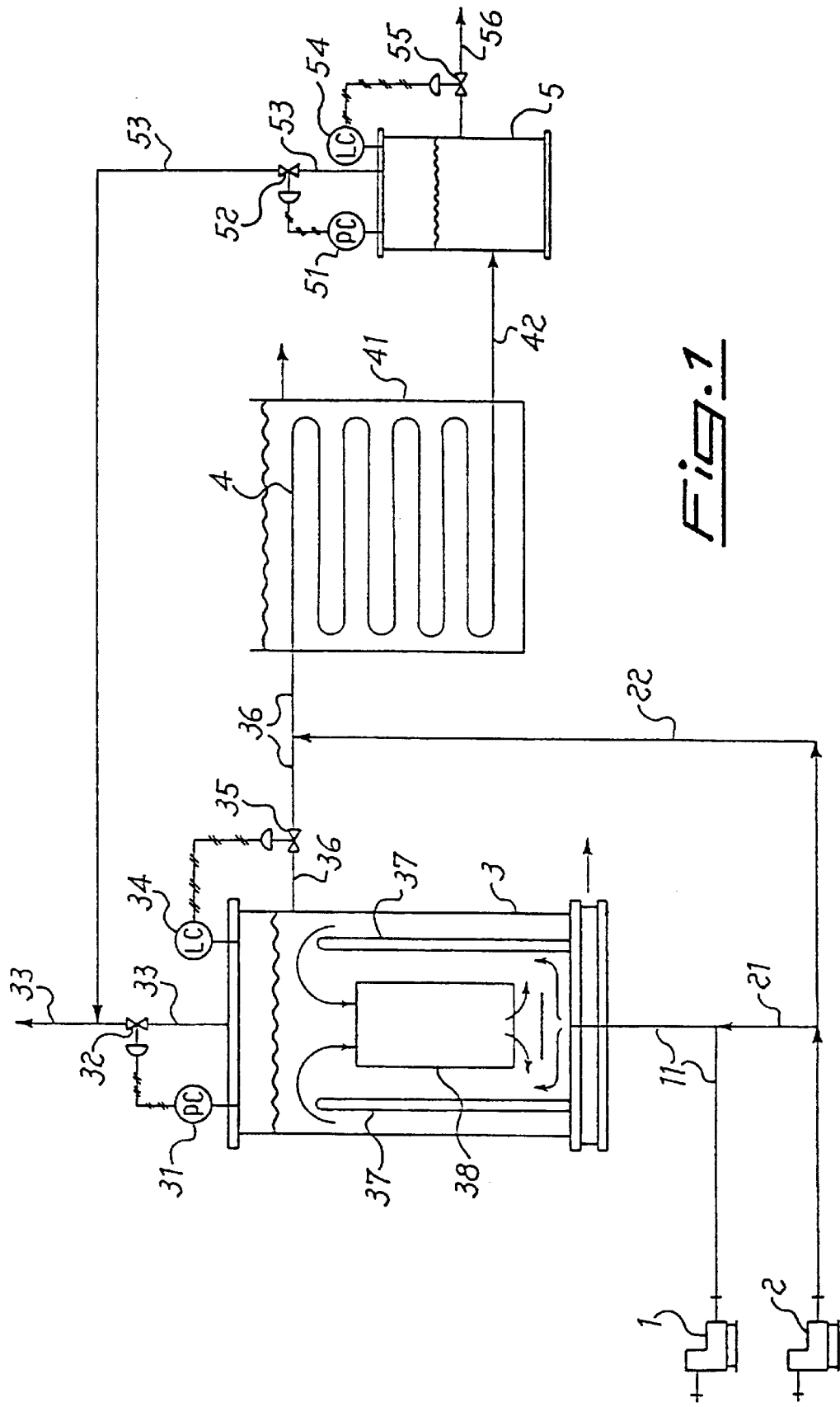
FIG. 1 is a schematic diagram of the process for manufacture of melamine in accordance with one embodiment of this invention.

Reference is made to FIG. 1 wherein a reaction scheme for melamine manufacture from urea is illustrated consisting of a first step reactor 3 combined with a second step reactor 4.

First step reactor 3 is kept under operating pressure by means of a pressure regulator 31 which, acting on the control value 32, ensures a controlled discharge of the reaction gas products through line 33. Said gases consist of ammonia and carbon dioxide in an approximate ratio of two moles of ammonia per mole of carbon dioxide. Said gases are saturated with melamine vapors. The first step reactor 3 is continuously fed, through line 11, with molten urea, which has been compressed up to reaction pressure by means of pump 1. Through line 21 and pump 2, liquid ammonia is conveyed into line 1, in order to keep constant the urea feeding to the reactor, thereby avoiding any possible generation of plugging as a result of urea decomposition due to reactor high temperature.

The correct temperature value in the first reaction step is ensured by molten salt circulation inside exchange tubes 37 fully plunged into the liquid reaction mixture. In this example, the reaction temperature is kept at 385° C. Inside the reactor, the molten reaction mixture is subject to fast movement around central conveyor tube 38 because of the evolution of ammonia and carbon dioxide gases during the reaction. Said gases are relatively poorly soluble in the liquid mass and therefore they go up along the reactor within the annular space between the conveyor tube and the wall of the reactor itself where molten salt heating tubes 37 are located. Said gases, after having reached the reaction liquid mixture upper surface, evolve and are conveyed outside the reactor through line 33 and valve 32 whose opening is controlled by pressure regulator 31 to keep the reactor under programmed operating pressure.

A liquid sensor level 34, placed inside the reactor, allows maintaining constant the reactor liquid level by acting upon valve 35 to discharge through line 36 an amount of liquid corresponding to the reactant volume fed to reactor.

Outlet line 36 is placed in a portion of the reactor beneath the liquid level, as a result of which it may discharge only a liquid phase essentially consisting of melamine containing a certain amount of unreacted urea, polycondensates, OAT, beyond a very little amount of dissolved ammonia and carbon dioxide.

Line 36 is connected to the second reaction step comprising a tubular reactor 4 fully plunged into a molten salt bath 41, ensuring a homogeneous reaction temperature all along the reactor.

Line 22 runs into line 36 downstream of valve 35. Line 22, by means of pump 2, ensures an ammonia inlet into reactor 4 to maintain a constant ammonia saturation of reactor liquid volume, in spite of ammonia consumption due to the reaction of the latter with polycondensates and OAT.

Ammonia coming from pump 2 to feed both reaction steps through line 21 and 22 is vaporized and superheated up to the reaction temperature by suitable heat exchange means not illustrated in the drawing.

Reaction mixture going through the second reaction step resides inside the reactor 4, under defined temperature and pressure conditions, for a period of time depending on the tubular reactor length and the liquid linear velocity.

At the outlet of reactor 4, reaction liquid mixture, through line 42, enters the gas/liquid separator 5 where liquid melamine is separated from gases, essentially comprising ammonia containing a small amount of carbon dioxide; said gases are conveyed through line 53 into line 33. Valve 52, controlled by pressure regulator 51, maintain separator 5 under a pressure very close to that of the first step reactor 3. The pressure in separator 5 is, however, lower than the pressure of the first step reactor 3 so as to allow the liquid mass, coming, from line 36 and passing through the second step reactor 4, to reach gas/liquid separator 5, overcoming the friction losses of the second step reactor 4, lines 36 and 42 and valve 35.

Liquid melamine is collected from separator 5 through line 56 by means of control valve 55, which is controlled by level sensor 54, so as to keep a constant level in separator 5.

8,230 Kg/h of urea and 410 Kg/h of ammonia are fed to the first step reactor as discussed above.

Reaction pressure is maintained at a fixed value of $8 \times 10^3$ kPa by discharging, under pressure control, about 5,700 Kg/h off-gas consisting of 46% ammonia by weight, 50% carbon dioxide by weight and about 4% melamine vapor by weight. Melamine vapor is totally recovered and injected again into the reaction zone by means of a conventional off-gas cooling unit and melamine adsorption using the urea stream charged to the reactor. The melamine recovery unit is not illustrated in the drawing. Recovered melamine, in an amount of about 220 Kg/h, returns to the reactor through line 11 and therefore any loss of yield is avoided.

Reaction temperature is kept at an average value of 385° C. by the circulation of molten salts fed to the reactor at a flow rate of 430 m³/h at a temperature of 420° C. Outlet temperature of the reactor 3 is 410° C. due to endothermic nature of the reaction.

At the exit of first step reactor 3 (line 36) the following products are

| melamine | 2,709 kg/h |
| unreacted urea | 75 kg/h |
| OAT | 110 kg/h |
| polycondensates | 60 kg/h |
| dissolved ammonia | 40 kg/h |
| dissolved carbon dioxide | 25 kg/h |

Melamine to urea conversion according to the overall reaction stoichiometry (see equation 7) is 94% and melamine purity degree excluding gaseous products (ammonia and carbon dioxide) is 91.7%. 150 kg/h of ammonia is added to the liquid mixture coming out of the first step reactor 3 before entering the second step reactor 4.

The second step reactor 4 comprises a tube 234 m long with an internal diameter of 5 cm. Fluid linear velocity inside the tube is 35 cm/sec., with the Reynolds number being 17,700.

The thermostatic vessel is kept at 420° C. using the same molten salts as in the first step reactor 3 and the amount of heat associated to chemical reactions taking place in second step reactor 4 is practically negligible. Pressure is fixed at $7.5 \times 10^3$ kPa in order to compensate for the pressure drop due to valve 35. Under the above conditions, 2,880 kg/h of degassed melamine are obtained having a purity of 99.64% (excluding gaseous products).

The overall reaction yield is 99.62%.

EXAMPLE 2

Figure 2:
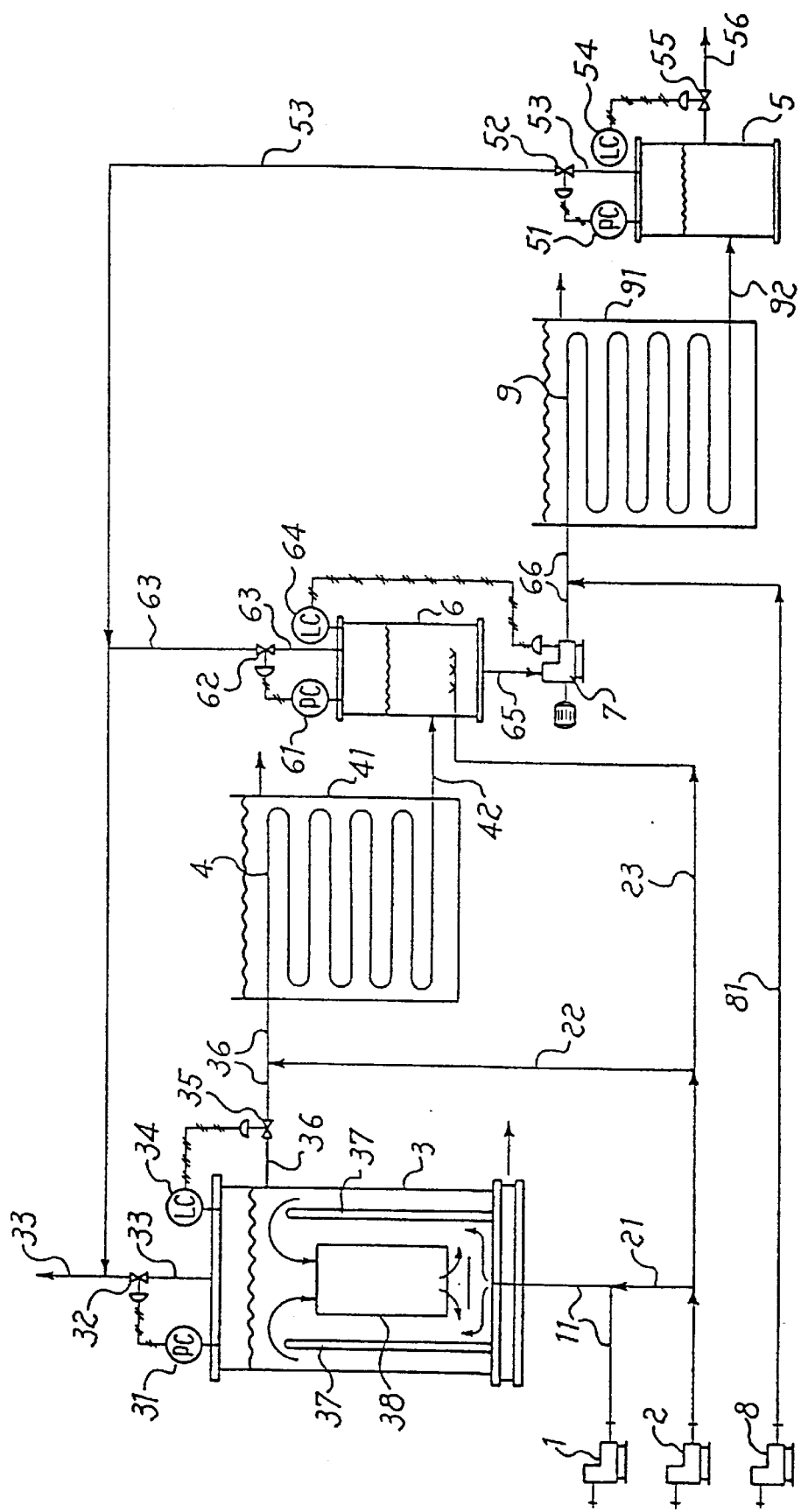
FIG. 2 is a schematic diagram of the process for manufacture of melamine in accordance with another embodiment of this invention.

FIG. 2 illustrates a melamine reaction unit starting from urea equipped with a second reaction step comprising two reactors in accordance with one embodiment of this invention.

Tubular reactor 4 is operated at the same temperature and pressure conditions as in the second reaction step of Example 1, while tubular reactor 9 is operated at a higher pressure ranging between $8 \times 10^3$ kPa and $30 \times 10^3$ kPa and includes the removal of carbon dioxide from the reaction mixture coming out of tubular reactor 4. In this Example, the pressure is $20 \times 10^3$ kPa. The first step reactor 3 is kept under the same conditions as in Example 1:

| temperature | 385° C. |
| pressure | $8 \times 10^3$ kPa |
| urea flow rate (pump 1, line 11) | 8230 kg/h |
| ammonia linear velocity (pump 2, line 21) | 410 kg/h |

From the outlet of the first step reactor 3, a liquid phase is obtained having the following composition:

| melamine | 2714 kg/h |
| unreacted urea | 75 kg/h |
| OAT | 110 kg/h |
| polycondensates | 60 kg/h |
| dissolved ammonia | 40 kg/h |
| dissolved carbon dioxide | 25 kg/h |

The above liquid phase is fed, through line 36, to tubular reactor 4 together with 75 kg/h ammonia coming, from pump 2 through line 22.

The outcoming stream from tubular reactor 4 (line 42) contains 71 kg/h $CO_2$ partly, namely 25 kg/h, deriving from the liquid reaction mixture entering tubular reactor 4, and partially (46 kg/h) as a result of conversion to melamine of urea and OAT coming out of the first step reactor 3.

Pressure and temperature of tubular reactor 4 is, as in Example 1, $7.5 \times 10^3$ kPa and 420° C. respectively. Tubular reactor 4 comprises a tube, 234 meter long with an internal diameter of 5 cm, wherein the reaction mixture passes with a linear velocity of 35 cm/sec, with the Reynolds number being 17,700. Tubular reactor 4 effluent contains raw melamine having a purity degree better than 99%, besides ammonia that is partly in the gaseous state and partly dissolved as well as carbon dioxide, 80% of which is present as a gas phase with ammonia. This effluent, through line 42, enters stripping tower 6, where, after gas phase removal including most of the carbon dioxide, the liquid phase is subject to a dissolved carbon dioxide stripping by scrubbing said liquid phase with 200 kg/h gaseous ammonia at 420° C., coming from pump 2 and line 23.

Pressure is maintained constant at the value of $7.5 \times 10^3$ kPa in the tower by means of the pressure regulator 61 which, acting on valve 62, discharges cases into an off-gas duct through line 63.

Liquid phase coming out of stripping tower 6 through line 65 consists of a 2935 kg/h raw melamine stream 99% pure, containing 50 kg/h dissolved ammonia. Effluent stripping from tower 6 is practically free from carbon dioxide.

Stripping tower 6 liquid level is kept constant by means of level control 64 acting on the flow rate of the extraction and compression pump 7, which is connected with stripping tower 6 through line 65 on one side and tubular reactor 9 through line 66 on the other side. Pump 7 is designed to raise the pressure of tubular reactor 9 to $20\times10^3$ kPa to allow a fast conversion into melamine of polycondensates which have not been converted in tubular reactor 4. For this purpose, 250 kg/h of superheated gaseous ammonia coming from line 66 are injected into tubular reactor 9 through line 81 by means of a second ammonia pump 8 before the introduction of raw melamine. Ammonia vaporization and superheating devices in lines 21 to 23 and 81 are not shown in the drawing to simplify the overall reaction scheme.

Reactor 9 is kept at 420° C. by a molten salt bath 91. Reactor 9 consists of an 8 cm internal diameter, 92 meter long tube, in which the liquid phase passes through at a 14 cm/sec linear velocity corresponding to a Reynolds number of 11,000.

High purity melamine comes out of tubular reactor 9 through line 92, then it passes to gas/liquid separator 5 where gaseous ammonia is sent to off-gas duct 33 through line 53, under the pressure control provided by the system pressure regulator 51 and valve 52.

Through line 56, under the level control provided by the system level sensor 54 and valve 55, liquid mixture containing 2880 kg/h of pure melamine (>99.9%) is recovered together with 150–160 kg/h dissolved ammonia.

Reaction yield, referred to overall equation (7), is practically 100%.

What is claimed is:

1. A high-pressure melamine manufacturing process starting from urea and having high yields and conversion rates comprising the steps of:
   a) feeding urea to a first reactor containing molten melamine, said first reactor operating continuously and being kept at a temperature in a range of 360 to 420° C. and at a pressure higher than about $7\times10^3$ kPa while a vigorous mixing is provided by evolving gases;
   b) recovering a reaction liquid product comprising 85 to 95% melamine and removing a gaseous phase comprising $CO_2$ and $NH_3$;
   c) feeding said recovered reaction liquid product continuously together with fresh $NH_3$ to a first tubular reactor, whereby a substantially whole volume of said tubular reactor is occupied by the recovered reaction liquid product without any mixing of the reaction liquid product with any reactants or intermediate products, said recovered reaction liquid product is maintained at a temperature in a range of 360 to 450° C. and at a pressure higher than about $7\times10^3$ kPa for a residence time sufficient to complete a reaction; and
   d) collecting melamine from an outlet of the first tubular reactor.

2. A high-pressure melamine manufacturing process according to claim 1, wherein an amount of fresh ammonia to be fed to the first tubular reactor together with the reaction liquid product is higher than a sum of an amount corresponding to a reaction liquid product saturation plus a stoichiometric amount necessary to convert all OAT and all polycondensates to melamine, the amount of said ammonia being sufficient to ensure a substantial excess ammonia within the recovered reaction liquid product.

3. A high-pressure melamine manufacturing process according to claim 1, wherein the reaction step c) comprises said first tubular reactor and a second tubular reactor wherein at an outlet of the first tubular reactor, a gaseous phase comprising ammonia, carbon dioxide and melamine vapor traces is removed and molten melamine is fed, together with fresh ammonia and after removal of dissolved carbon dioxide, to the second tubular reactor, the pressure within the second tubular reactor being higher than the pressure of both the first reactor and the first tubular reactor.

4. A high-pressure melamine manufacturing process according to claim 3, wherein the pressure in the second tubular reactor is between about $8\times10^3$ and $30\times10^3$ kPa.

5. A high-pressure melamine manufacturing process according to claim 3, wherein a third reaction section, similar to the reaction step c), is added to the reaction step c).

6. A high-pressure melamine manufacturing process according to claim 1, wherein the first tubular reactor and the second tubular reactor comprise geometrical parameters to ensure a Reynolds number higher than 5,000.

7. A high-pressure melamine manufacturing process according to claim 1, wherein said first tubular reactor and said second tubular reactor are heated by immersion in a molten salt bath.

8. A high-pressure melamine manufacturing process according to claim 2, wherein the reaction step c) comprises said first tubular reactor and a second tubular reactor wherein at an outlet of the first tubular reactor, a gaseous phase comprising ammonia, carbon dioxide and melamine vapor traces is removed and molten melamine is fed, together with fresh ammonia and after removal of dissolved carbon dioxide, to the second tubular reactor, the pressure within the second tubular reactor being higher than the pressure of both the first reactor and the first tubular reactor.

9. A high-pressure melamine manufacturing process according to claim 8, wherein the pressure in the second tubular reactor is between about $8\times10^3$ and $30\times10^3$ kPa.

10. A high-pressure melamine manufacturing process according to claim 8, wherein a third reaction section, similar to the reaction step c), is added to the reaction step c).

11. A high-pressure melamine manufacturing process according to claim 9, wherein a third reaction section, similar to the reaction step c), is added to the reaction step c).

12. A high-pressure melamine manufacturing process according to claim 9, wherein the first tubular reactor and the second tubular reactor comprise geometrical parameters to ensure a Reynolds number higher than 5,000.

13. A high-pressure melamine manufacturing process according to claim 12, wherein said first tubular reactor and said second tubular reactor are heated by immersion in a molten salt bath.

* * * * *